United States Patent [19]

Hafner

[11] Patent Number: 4,551,430

[45] Date of Patent: Nov. 5, 1985

[54] CONSTITUTIVE PRODUCER OF A THERMOSTABLE GLUCOSE ISOMERASE

[75] Inventor: Edmund W. Hafner, Arlington Heights, Ill.

[73] Assignee: UOP Inc., Des Plaines, Ill.

[21] Appl. No.: 546,132

[22] Filed: Oct. 27, 1983

[51] Int. Cl.$^4$ .................. C12P 19/24; C12N 9/92; C12N 1/20; C12R 1/465
[52] U.S. Cl. ..................... 435/94; 435/234; 435/253; 435/886
[58] Field of Search .................. 435/94, 253, 234

[56] References Cited

U.S. PATENT DOCUMENTS

Re. 29,152   3/1977   Armbruster et al. .............. 195/31 F
4,355,103   10/1982   Boguslawski et al. ........... 435/94 X

OTHER PUBLICATIONS

American Type Culture Collection (ATCC) Catalogue of Strains I, 15th Ed., 1982, p. 227.
W. P. Chen, Process Biochemistry, Jun./Jul., 1980, pp. 30-35.

Primary Examiner—Lionel M. Shapiro
Attorney, Agent, or Firm—Thomas K. McBride; William H. Page, II; Eugene I. Snyder

[57] ABSTRACT

A mutant *Streptomyces thermoviolaceus,* NRRL 15615, elaborates a thermostable glucose isomerase in high yield, constitutively. The GI produced shows a negligible loss in activity when heated at 90° C. in high fructose corn syrup for 5 minutes relative to the same treatment at 80° C. The mutant microorganism produces about 1500 units of glucose isomerase per gram of dry weight cells in the absence of xylose.

6 Claims, No Drawings

CONSTITUTIVE PRODUCER OF A THERMOSTABLE GLUCOSE ISOMERASE

Glucose isomerase, sometimes referred to as xylose isomerase, catalyzes the reversible isomerization of glucose to fructose. Fructose long has been recognized as a good alternative to sugar (sucrose) because of its relatively high sweetness and other desirable physical, chemical, and physiological properties, and the use of glucose isomerase to convert glucose in corn syrup to fructose has been practiced for some time. Although the production of high fructose corn syrup is concentrated in the United States, plant capacity in Europe and the Far East has been steadily increasing.

The enzyme glucose isomerase occurs widely in nature and is produced by such genera as Pseudomonas, Lactobacillus, Actinoplanes, Arthrobacter, Bacillus, and Streptomyces, with the latter species being perhaps the most important commercial source of the enzyme (W.-P. Chen, Process Biochemistry, June/July, 1980, pages 30-35). The need for improving glucose isomerase (GI) production over that found in wild-type microorganisms has spurred many efforts to produce mutants with improved characteristics. For example, U.S. Pat. No. Re. 29,152 describes mutants of Streptomyces olivochromogenes which have the characteristics of (1) producing GI in the absence of xylose (i.e., the enzyme is constitutive), but (2) exhibits greater GI production in the presence of xylose (i.e., enzyme production is induced, at least in part), and (3) in the presence of xylose the mutant produces more GI than the parent.

A desirable GI producing microorganism would produce the enzyme constitutively, that is, the microorganism would elaborate GI when grown on a medium free of xylose. This is advantageous because of the relatively high cost of xylose. A desirable GI producer also should be characterized by relatively high enzyme production, especially as measured by GI activity per unit of dry weight cells. Additionally, such a GI producer should show a high growth rate, so as to have high enzyme production per unit time. Another desirable characteristic would be production of a thermostable GI. A thermophilic GI producer would have added benefits of a rapid growth rate and lower susceptibility to microbial contamination during fermentation because of a higher culture temperature. Lastly, it is desirable that the GI producer grow well in common, inexpensive media, that is, growth requirements for the microorganism should be such that relatively inexpensive sources of carbon, nitrogen, and minerals can be used.

We have discovered a mutant of the thermophilic strain Streptomyces thermoviolaceous possessing the aforementioned desirable and advantageous properties. In particular, the mutant described herein produces GI constitutively. The mutant also produces as much GI in the absence of xylose as in the presence of that sugar. Additionally, the mutant produces considerably more Gi in the absence of xylose than does the parent strain in the presence of xylose. The mutant described herein grows well in common media and has no unusual growth requirements, and the GI it elaborates is far more resistant to heat than other common isomerases.

SUMMARY OF THE INVENTION

The object of this invention is to obtain a microorganism which elaborates a thermostable glucose isomerase constitutively in good yield. An embodiment is a biologically pure culture of mutant microorganisms of Streptomyces thermoviolaceous having the ability to produce a thermostable glucose isomerase when the mutant microorganisms are grown aerobically in a medium containing an assimilable source of carbon, nitrogen, and mineral nutrients at a temperature from about 20° to about 55° C. In a more specific embodiment the mutant is Streptomyces thermoviolaceous NRRL 15615.

DESCRIPTION OF THE INVENTION

The core of this invention is the induction and selection of a mutant strain of Streptomyces thermoviolaceous which produces a glucose isomerase constitutively, which elaborates glucose isomerase in high yeild, and whose glucose isomerase exhibits superior thermal stability. The starting point of this invention was the screening of various thermophilic organisms for glucose isomerase activity.

EXAMPLE 1—Thermophilic Streptomyces Strains

The maintenance medium (SCM) for all microorganisms herein consisted of 1% yeast autolysate, 1% casein enzymatic hydrolysate, 0.5% beef extract, 1 millimolar magnesium sulfate, and 0.05 molar potassium phosphate with the pH adjusted to 7.10 with sodium hydroxide before autoclaving. Bacteria were transferred regularly onto a 2% agar medium containing the above ingredients as an inoculum for liguid cultures. The strains were generally incubated for 48 hours in a liquid culture at 45° C. for thermophilic organisms, 30° C. otherwise, with agitation (200 rpm) in a New Brunswick Controlled Environment Shaker.

After 48 hours, the 50 ml cultures (contained in 250 ml baffled Erlenmeyer flasks) were harvested and washed free of spent culture broth by centrifugation (4° C. at 15,000 rpm for 10 minutes). A portion of the cell pellet was dried by microwave and % solids calculated, using a CEM Corp. Model AVC-MP instrument. The remaining (wet) cells were resuspended in 30 ml of 0.02 M potassium phosphate buffer, pH 7.0, containing 0.85% sodium chloride. This material was sonicated for 1 minute at low power with a Labline sonifier.

For the glucose isomerase assay procedure, 0.2 ml of the sonicated cell slurry was diluted to 1 ml with distilled $H_2O$. This 1 ml sample was added to 3 mls of the substrate solution which consists of 45% fractose (W/V), 0.05 M imidazole buffer at pH 7.5, $5 \times 10^{-3}$ M $MgSo_4$, and $5 \times 10^{-4}$ M $CoCl_2$. After thorough mixing, the reaction mixture was incubated at 60°C. for a 60 minute duration. The reaction was terminated by quenching with the addition of 1 ml of 0.1 N HCl with mixing, and chilling on ice. The enzyme activity was determined by measurement of glucose concentration using a Beckman Glucose Analyzer. One unit of GI activity is equivalent to the formation of 1 umole of glucose per ml per minute.

Cultures of Streptomyces thermovulgaris, ATCC 19284, and Streptomyces thermoviolaceus, ATCC 19283, were examined for glucose isomerase production with the results summarized in the following table.

TABLE 1

| Glucose Isomerase Activity of Thermophilic Streptomyces | | |
|---|---|---|
| | GI activity, units/g dry weight cells | |
| Strain | No xylose | 0.5% xylose added |
| S. thermovulgaris. ATCC 19284 | ca. 10 | 190 |
| S. thermoviolaceus. | ca. 10 | 60 |

TABLE 1-continued

| Glucose Isomerase Activity of Thermophilic Streptomyces | | |
|---|---|---|
| | GI activity, units/g dry weight cells | |
| Strain | No xylose | 0.5% xylose added |
| ATCC 19283 | | |

As the table shows, both thermophilic organisms produce glucose isomerase at relatively low levels even with xylose in the growth medium.

Having selected two thermophilic microorganisms which are GI producers, it was necessary to determine the thermal stability of their glucose isomerase, especially relative to other isomerases. For the purpose of this application, a thermostable GI is one which loses less than 10% of its isomerase activity when heated for 5 minutes at 90° C. in a solution of 42% fructose at pH 7.0 relative to its activity after heating for 5 minutes at 80° C. under otherwise identical conditions.

EXAMPLE 2—THERMAL STABILITY OF VARIOUS GLUCOSE ISOMERASES

Crude extracts of glucose isomerase were prepared by sonication of harvested wet cells with subsequent dialysis into 0.1 molar potassium phosphate, pH 7.0, containing 1 millimolar magnesium sulfate. Table 2 summarizes the results when thermal stability was measured in a phosphate buffer at pH 7.0. In all cases the enzyme solution was heated at the indicated temperature for 5 minutes.

TABLE 2

| Thermal Stability of Various GI's in Phosphate Buffer | | |
|---|---|---|
| | GI activity (% of original) after 5 minutes heating at | |
| Strain | 80° C. | 90° C. |
| S. alboduncus (ATCC 14698) | 84 | 4 |
| S. albovinaceus (ATCC 15823) | 72 | 10 |
| S. omiyaensis (ATCC 27454) | 53 | 4 |
| S. thermoviolaceus (ATCC 19283) | 98 | 60 |
| Actinoplanes missouriensis (NRRL B 3342) | 103 | 23 |
| S. thermovulgaris (ATCC 25501) | 78 | 6 |

As the table clearly shows the isomerase from S. thermoviolaceus is by far the most stable to heat denaturation of those tested. Since it was previously known that thermostability in fructose solutions does not always parallel that observed in a dilute phosphate buffer, thermostability was determined by heating crude GI extracts in a solution of 42% fructose at pH 7.0. Results are summarized in the following Table 3.

TABLE 3

| Thermal Stability of Various GI's in High Fructose Corn Syrup | | |
|---|---|---|
| | GI activity (% of original) after 5 minutes heating at | |
| Strain | 80° C. | 90° C. |
| S. alboduncus (ATCC 14698) | 82 | 59 |
| S. albovinaceus (ATCC 15823) | 92 | 71 |
| S. omiyaensis (ATCC 27454) | 120 | 84 |
| S. thermoviolaceus (ATCC 19283) | 69 | 69 |
| A. missouriensis (NRRL B 3342) | 90 | 76 |

These data clearly show little, if any, additional loss of activity resulting from heating GI from S. thermoviolaceus at 90° C. as compared to 80° C., thereby demonstrating the superior thermal stability of the GI from this species relative to the other enzymes examined.

Having demonstrated the superior thermal stability of the GI from S. thermoviolaceus, it was now desired to obtain a mutant strain which overproduced glucose isomerase constitutively.

EXAMPLE 3—Mutagenesis

Mutagenesis was begun using the parent strain Streptomyces thermoviolaceus, ATCC 19283, in a liquid culture broth for approximately 24 hours. Ten ml of the culture was washed free of broth under sterile conditions and the wet cell pellet was resuspended in 10 ml of 0.2 M tris(hydroxymethylamino)methane hydrochloride at a pH of 7.5. Ethyl methanesulfonate was added to the cell suspension in a concentration of 0.15 ml per 10 ml suspension and the cells were then incubated, with agitation, at 30° C. for 2.5 hours. After this time the EMS treated cells were added to 50 ml of the maintenance medium and permitted to grow for 48 hours.

Screening of the mutagenized cells involved transferring the organisms from liquid cultures to agar plates so that individual colonies could be evaluated for enzyme production. To achieve this, 2.5 ml aliquots of the liquid culture were briefly (10 seconds) sonicated at low power. This procedure breaks up the mycelial strands and releases individual mutated cells. These aliquots were then recombined and diluted to a concentration of 40% glycerol and stored at −70° C. until used.

Dilutions of these EMS treated cells were then plated onto an agar medium to give approximately 200 colonies per plate. These colonies were assayed for constitutive production of glucose isomerase. The mutant microorganism Streptomyces thermoviolaceus NRRL 15615 was founded by this procedure. Comparison of GI production by the parent and mutant strains are shown in the accompanying table.

TABLE 4

| Comparison of GI Production | | |
|---|---|---|
| Microorganism | 1.0% Xylose | GI, units/g dry cells |
| ATCC 19283, parent | present | 60 |
| | absent | 10 |
| NRRL 15615, mutant | present | 1500 |
| | absent | 1500 |

Medium optimization for glucose isomerase production by the mutant strain NRRL 15615 was performed by adding xylose, corn steep liquor, or yeast extract to a base medium which contained 50 mM phosphate buffer, pH 7.0, 3 mM MgSO$_4$, 2 g/L NaNO$_3$, 1 mM CaCl$_2$, and 2 g/L (NH$_4$)$_2$SO$_4$. Results are shown in the following table.

TABLE 5

| Medium Optimization for GI Production by S. Thermoviolaceus, NRRL 15615 | | | | |
|---|---|---|---|---|
| Addend (1%) | Presence/Absence | | | |
| Xylose | + | − | + | − |
| Corn steep liquor | + | + | − | + |
| Yeast extract | + | + | + | − |
| GI activity, units/g dry weight | 1500 | 1500 | 1000 | 1100 |

Morphological characteristics of the parent strain and its mutant in various media after 3 days at 42° C. are summarized in Table 6.

TABLE 6

Morphology of S. Thermoviolaceus

| Medium (agar-based, 20 g/l) | ATCC 19283 | NRRL 15615 |
|---|---|---|
| 1. SCM | 1–2 cm flat colonies, deep violet; aromatic, almost pleasing odor; white coating covering most colonies | same |
| 2. LB[a] | 0.5 cm flat colonies; no color or odor | same |
| 3. malt extract[b] | Isolated single colonies were white, crowded colonies were yellow, dense inoculum smear was violet; aromatic odor | same |
| 4. M9 + casamino acids[c] | 1 cm colonies, volcanic shape, surrounded by black-gray color | similar, but color more whitish-gray |
| 5. M9 + dextran[d] | no significant growth over M9 salts alone (i.e., no dextran supplementation); very faint, flat, 0.5 cm colonies | same |

[a]Contains per liter 10 g tryptone, 5 g yeast extract, and 10 g NaCl.
[b]Bacto malt extract agar prepared per manufacturer's (Difco) instructions.
[c]Contains per liter 6 g $Na_2HPO_4$, 3 g $KH_2PO_4$, 0.5 g NaCl, 1 g $NH_4Cl$; plus $MgCl_2$ (1 mM), $CaCl_2$ (0.1 mM), and 2 g casamino acids.
[d]Similar to that above, with 1% dextran replacing the casamino acids.

Table 6 shows the mutant and parent strains manifest essentially similar growth morphology on five different media. In lieu of testable genetic markers, this is the most convincing evidence that the mutant strain is indeed derived from the parent strain and is not a fortuitous contaminant.

The glucose isomerase from the mutant microorganism of this invention may be used to isomerize glucose to fructose. This may be done either homogeneously, where a solution of GI and glucose are permitted to remain in contact for a sufficient time to achieve the desired conversion, or heterogeneously, where the enzyme is supported on a suitable matrix and a solution of glucose is contacted with the immobilized enzyme, which is generally as a fixed bed. Contact temperatures from about 40° C. to about 90° C. are common, with a temperature between about 50° and 80° C. more desirable for the thermostable GI of this invention. Such isomerization is conducted at a pH between about 6.5 and 9.5, and more usually between about 7.0 and 8.5. The fructose is then recovered by suitable means, as by chromatographic absorption.

What is claimed is:

1. A biologically pure culture of a mutant of *Streptomyces thermoviolaceus* NRRL 15615 having the ability to produce a thermostable glucose isomerase as a constitutive enzyme when the mutant microorganisms are grown aerobically in a medium containing an assimilable source of carbon, nitrogen, and mineral nutrients at a temperature from about 20° to about 55° C.

2. A method of producing a thermostable glucose isomerase comprising cultivating *Streptomyces thermoviolaceus* NRRL 15615 in a nutrient medium for a time sufficient to produce a recoverable quantity of the isomerase.

3. The method of claim 2 where the medium is devoid of xylose.

4. A method of converting glucose to fructose comprising contacting an aqueous solution containing glucose with a glucose isomerase from *Streptomyces thermoviolaceus* NRRL 15615 at a temperature from about 40° to about 90° C. at a pH between about 6.5 and 9.5 for a time sufficient to effect the isomerization of glucose to fructose, and recovering the formed fructose.

5. The method of claim 4 where the temperature is from about 50° to about 80° C.

6. The method of claim 4 where the pH is from about 7.0 to about 8.5.

* * * * *